United States Patent [19]
Gougelet

[11] Patent Number: 5,568,662
[45] Date of Patent: Oct. 29, 1996

[54] SPINAL/CERVICAL IMMOBILIZATION DEVICE AND METHOD

[76] Inventor: Robert M. Gougelet, 165 Wagner La., Corrales, N.M. 87048

[21] Appl. No.: 225,055

[22] Filed: Apr. 8, 1994

[51] Int. Cl.$^6$ ...................................................... A61G 1/00
[52] U.S. Cl. ................................. 5/625; 5/628; 128/870
[58] Field of Search ........................... 5/621, 622, 625, 5/628, 627; 128/869, 870

[56] References Cited

U.S. PATENT DOCUMENTS

| | | | |
|---|---|---|---|
| 2,511,061 | 6/1950 | Hughes | 5/628 X |
| 2,675,564 | 4/1954 | Hughes | 5/628 X |
| 3,449,776 | 6/1969 | Brock | 5/627 |
| 3,609,778 | 10/1971 | Zeiner | 5/628 |
| 4,252,113 | 2/1981 | Scire | 128/870 X |
| 5,088,137 | 2/1992 | Rose | 5/625 |
| 5,179,746 | 1/1993 | Rogers | 5/628 X |
| 5,274,864 | 1/1994 | Morgan | 5/625 X |

FOREIGN PATENT DOCUMENTS

| | | | |
|---|---|---|---|
| 0025672 | 1/1988 | European Pat. Off. | 5/628 |
| 3021871 | 11/1993 | WIPO | 128/869 |

*Primary Examiner*—Michael F. Trettel
*Attorney, Agent, or Firm*—Deborah A. Peacock; Jeffrey D. Myers

[57] ABSTRACT

A spinal and cervical immobilization apparatus (and associated methods) combining a fiber-reinforced, resin transfer molded, spinal immobilization board having rows of slots at one end with head and neck support brackets fitting into the slots, as required by the width of the patient's head and neck. The board has rounded and upturned corners, molded grip holes with finger indentations, and beveled indentations for the head and torso of a patient into which fit padding, and is 1.75" or less in thickness, weighs nine pounds or less, and can carry 700 pounds without cracking.

57 Claims, 4 Drawing Sheets

SPINAL/CERVICAL IMMOBILIZATION DEVICE AND METHOD

BACKGROUND OF THE INVENTION

1. Field of the Invention (Technical Field)

The present invention relates to apparatuses and methods for immobilizing in emergency situations the head, neck, and spinal column of patients with known or suspected spinal injury, and also permitting transport of such patients.

2. Background Art

Thousands of traumatic head and neck injuries occur each year in the United States, primarily as a result of automobile and motorcycle accidents, but also as a result of assault and recreational accidents. Patients with such injuries need to be immediately immobilized on a spinal immobilization board that restricts movement of the cervical, spinal, and head areas. Proper medical equipment to accomplish this is vital to safely move the patient from the accident scene.

Unfortunately, despite vastly improved treatments and technologies for treating spinal cord injuries, patients with traumatic head and neck injuries may receive secondary injuries as a result of poor post-traumatic handling, and all too often these are the result of poor carrying equipment (i.e., inadequate spinal immobilization boards and cervical devices). Many patients must lie for hours on an immobilization board during transport, x-ray clearance, x-rays and other procedures for medical evaluation and treatment, and this needs to be rendered as comfortable and medically secure as possible.

Traumatically injured patients should, under ideal circumstances, be examined by medical personnel either while at the accident scene, en route to a hospital, or immediately upon arrival at a hospital without having to move the patient an additional time from the immobilization board. Current cervical restraint devices preclude examination by a physician and must, therefore, be removed to perform needed examinations, creating an additional risk for the patient. The wood or plastic boards currently available may distort or block x-rays, again creating the need for removal of the patient from the immobilization device for a repeat x-ray. Each time a patient is moved on and off the board, a significant risk of secondary injury is presented.

The boards currently in use are susceptible to damage by exposure to weather, ultraviolet light, cracking, and by abrasion during handling and storage. The degradation of surfaces greatly increases the likelihood of entrapment of bacteria and reduces the strength of the boards. Plywood boards become rough and splinter (or even crack in two, dropping a patient to the ground) and plastic boards become burred and cracked, thereby losing structural integrity and creating the possibility of causing abrasions, puncture wounds, and slivers in the patient and/or rescuers.

Furthermore, the currently available boards are heavy and awkward to handle. Boards that are flat with a low profile cause the patient to be twisted and rocked as the trauma team attempts to get their fingers under the board to lift it. Boards that have a higher profile with easy hand holds require patients to be lifted higher in order to be placed on the board, again increasing risk to the patient.

Injection molded plastic devices have attempted to resolve the above issues with limited success. They still remain costly, heavy, and awkward to use and sometimes have unacceptable x-ray distortion. Without fiber reinforcement, they are either thick and heavy or too thin and too flexible.

Cervical spine immobilization has also seen no major improvements in the past several decades, although there has been an influx of cardboard and foam devices which are bulky, difficult to put on (often taking several precious minutes to secure), and which can easily be foiled by a patient who is trying to move his or her head. This is a particular problem with a patient who is under the influence of alcohol or otherwise resistant to the medically necessary physical restraints that must be imposed to reduce secondary spinal injuries. In addition, the disposable cardboard and foam devices are costly, with the total expense for the United States running several million dollars per year.

As demonstrated in Operation Desert Storm, there is an increased demand for military air lift and evacuation equipment and a need for high-performance trauma equipment. For airplane or helicopter transport, light-weight equipment which requires a small storage space is essential. Also a light-weight and fire resistant board would be particularly well suited for Air Rescue and mountain rescue services.

The present invention is of a fiber-reinforced, resin transfer molded, composite board incorporating a non-disposable cervical immobilization device. The many deficiencies of present technology cited above are largely obviated by the present invention.

SUMMARY OF THE INVENTION (DISCLOSURE OF THE INVENTION)

The present invention is of a spinal and cervical immobilization apparatus comprising: a board on which a body of a patient is placed and which comprises a plurality of bifurcated rows of bracket slots disposed at an end of the board; and a plurality of head and neck support brackets, each comprising a bracket slot engagement portion and a patient engagement portion. In the preferred embodiment the board is fabricated from a fiber-reinforced composite, preferably resin transfer molded, 1.75" or less in thickness (and most preferably 1.5" or less) and weighs nine pounds or less (but can carry up to 700 pounds without cracking), has upturned and rounded corners with molded grip holes therein, has a plurality of molded grip holes disposed near the edges thereof, the grip holes comprising indentations for fingers of persons carrying the board and patient, has beveled indentations for the head and torso of the patient, and has padding permanently, semi-permanently, or removably placed into the indentations. The board preferably has a plurality of bifurcated rows of bracket slots disposed at a central portion of the board and the invention includes a plurality of torso support brackets, each comprising a bracket slot engagement portion and a patient engagement portion.

The present invention is also of a spinal immobilization apparatus comprising a board on which a body of a patient is placed comprising a resin transfer molded, fiber-reinforced, composite, having a thickness of 1.75" or less (and most preferably 1.5" or less) and a weight of nine pounds or less (but can carry up to 700 pounds without cracking). In the preferred embodiment, the apparatus additionally comprises a cervical immobilization device comprising: a plurality of bifurcated rows of bracket slots disposed at an end of the board; and a plurality of head and neck support brackets, each comprising a bracket slot engagement portion and a patient engagement portion. Preferably, the corners of the board are upturned, the corners are rounded, and the corners have molded grip holes therein. A plurality of molded grip holes are preferably disposed near the edges of the board, the grip holes comprising indentations for fingers of persons carrying the board and patient. The board preferably also has beveled indentations for the head and torso of the patient and padding permanently, semi-permanently, or removably placed into the indentations. The board preferably has a plurality of bifurcated rows of bracket slots disposed at a central portion of the board and the invention includes a plurality of torso support brackets, each comprising a bracket slot engagement portion and a patient engagement portion. The cervical immobilization device alternatively may be a plurality of slidable head and neck engagement arms with a Y-shaped portion engaging the patient around but not covering the ears.

The present invention is also of a spinal immobilization apparatus comprising a board on which a body of a patient is placed comprising upturned corners and molded grip holes disposed in the upturned corners. In the preferred embodiment, the apparatus additionally comprises a cervical immobilization device comprising: a plurality of bifurcated rows of bracket slots disposed at an end of the board; and a plurality of head and neck support brackets, each comprising a bracket slot engagement portion and a patient engagement portion. The board is preferably fabricated from a fiber-reinforced composite, is resin transfer molded, is 1.75" or less in thickness (and most preferably 1.5" or less) and weighs nine pounds or less (but can carry up to 700 pounds without cracking). Preferably, the board comprises a plurality of molded grip holes disposed near the edges thereof, the grip holes comprising indentations for fingers of persons carrying the board and patient, beveled indentations for the head and torso of the patient, and padding permanently, semi-permanently, or removably placed into the indentations. The board preferably has a plurality of bifurcated rows of bracket slots disposed at a central portion of the board and the invention includes a plurality of torso support brackets, each comprising a bracket slot engagement portion and a patient engagement portion. The cervical immobilization device alternatively may be a plurality of slidable head and neck engagement arms with a Y-shaped portion engaging the patient around but not covering the ears.

The present invention is also of a spinal immobilization apparatus comprising a board on which a body of a patient is placed comprising a plurality of molded grip holes disposed near the edges thereof, the grip holes comprising indentations for fingers of persons carrying the board and patient. In the preferred embodiment, the apparatus additionally comprises a cervical immobilization device comprising: a plurality of bifurcated rows of bracket slots disposed at an end of the board; and a plurality of head and neck support brackets, each comprising a bracket slot engagement portion and a patient engagement portion. Preferably the board comprises a fiber-reinforced composite, is resin transfer molded, is 1.75" or less in thickness (and most preferably 1.5" or less) and weighs nine pounds or less (but can carry up to 700 pounds without cracking). Preferably, the corners of the board are upturned, the corners are rounded and comprise molded grip holes therein, the board has beveled indentations for the head and torso of the patient, and the apparatus additionally comprises padding means permanently, semi-permanently, or removably placed into the indentations. The board preferably has a plurality of bifurcated rows of bracket slots disposed at a central portion of the board and the invention includes a plurality of torso support brackets, each comprising a bracket slot engagement portion and a patient engagement portion. The cervical immobilization device alternatively may be a plurality of slidable head and neck engagement arms with a Y-shaped portion engaging the patient around but not covering the ears.

The invention is also of a spinal immobilization apparatus comprising: a board on which a body of a patient is placed comprising beveled indentations for the head and torso of the patient; and padding means permanently, semi-permanently, or removably placed into the indentations. In the preferred embodiment, the apparatus additionally comprises a cervical immobilization device comprising: a plurality of bifurcated rows of bracket slots disposed at an end of the board; and a plurality of head and neck support brackets, each comprising a bracket slot engagement portion and a patient engagement portion. Preferably, the board comprises a fiber-reinforced composite, is resin transfer molded, is 1.75" or less in thickness (and most preferably 1.5" or less) and weighs nine pounds or less (but can carry up to 700 pounds without cracking). Preferably, the corners of the board are upturned, the corners are rounded and comprise molded grip holes therein, and the board has a plurality of molded grip holes disposed near the edges thereof, the grip holes comprising indentations for fingers of persons carrying the board and patient. The board preferably has a plurality of bifurcated rows of bracket slots disposed at a central portion of the board and the invention includes a plurality of torso support brackets, each comprising a bracket slot engagement portion and a patient engagement portion. The cervical immobilization device alternatively may be a plurality of slidable head and neck engagement arms with a Y-shaped portion engaging the patient around but not covering the ears.

The invention is also of a method of immobilizing a patient's spinal and cervical areas, comprising: moving the patient onto a board comprising a plurality of bifurcated rows of bracket slots at an end thereof; placing a head and neck of the patient at a bifurcation of the rows; and setting head and neck support brackets in the slots such that both sides of the head and neck are engaged by the brackets. The board preferably also has a plurality of bifurcated rows of bracket slots disposed at a central portion of the board and torso support brackets are set in the slots such that both sides of the patient's torso are engaged by the brackets.

A primary object of the present invention is to provide an immobilization board that is light-weight and has a low thickness profile.

Another object of the invention is to reduce x-ray interference and thereby allow x-ray of a patient without removal from the board.

An additional object of the invention is to reduce cervical immobilization device interference with physician examination of the patient, permitting such examination without removal of the device.

Yet another object of the invention is to increase board service life and patient comfort.

Still another object of the invention is to eliminate the need for disposable cervical restraints used in conjuction with an immobilization board.

A primary advantage of the present invention is that its proper employment reduces occurrences of secondary spinal injury.

Another advantage of the present invention is a decreased risk to emergency workers from the board when transporting patients.

An additional advantage of the present invention is that the above-listed objects result in a device which saves time, space, and money for the individual rescue unit and hence for society as a whole.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODE FOR CARRYING OUT THE INVENTION)

The present invention is of a spinal/cervical immobilization device having the following most significant features: it comprises a board of dimensions approximately 72"×16"–18"×1.75" (or less, most preferably less than 1.5" in thickness) which is carbon-fiber-reinforced and fabricated by a resin transfer molding (preferably resin transfer molding) composite process and having a foam core; the ends (or corners) of the board are raised at an approximate seven degree angle to permit fingers to be placed under the ends of the board without rocking of the board; an end of the board has a plurality of slots disposed in two dimensions at an end of the board into which fit head and neck support brackets; and body support padding (preferably semi-soft, semi-permanent padding, e.g., polyurethane elastomer padding) is recessed in the board for patient comfort and stability.

Figure 1:
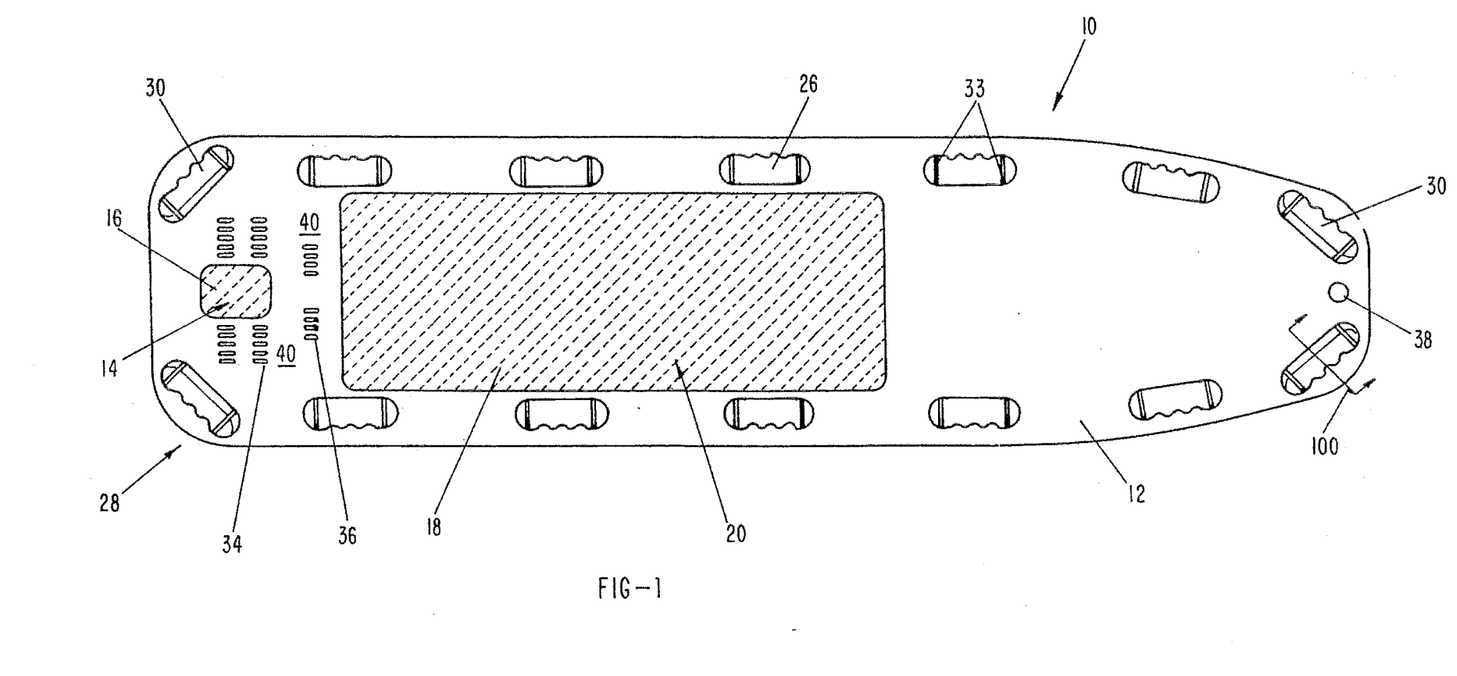
FIG. 1 is a top view of the preferred embodiment.

Referring to the top view of FIG. 1, the preferred immobilization device 10 comprises a fiber-reinforced composite body 12, a beveled edge head indentation 14, head padding 16, a beveled edge torso indentation 18, torso padding 20, edge molded grip holes 26, upraised corners 28, corner molded grip holes 30, head support bracket slots 34, neck support bracket slots 36, end hole 38, and board identification and serial number zone 39.

Figure 2:
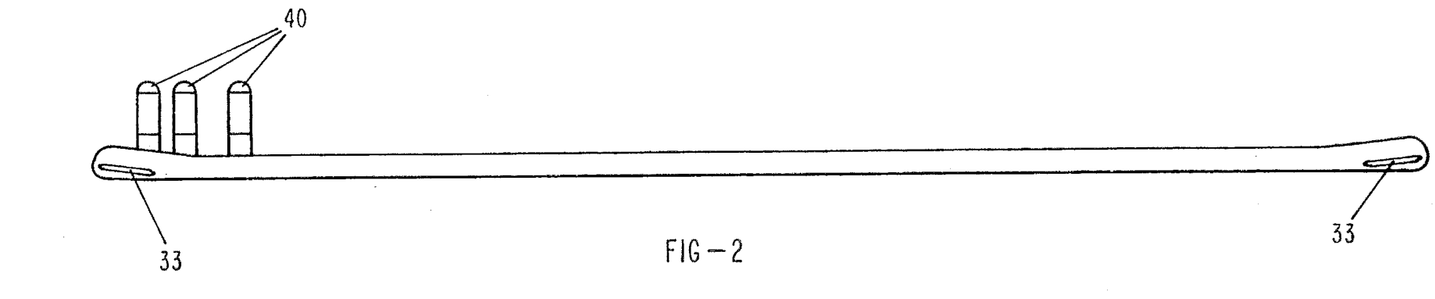
FIG. 2 is a side view of the preferred embodiment.
Figure 3:
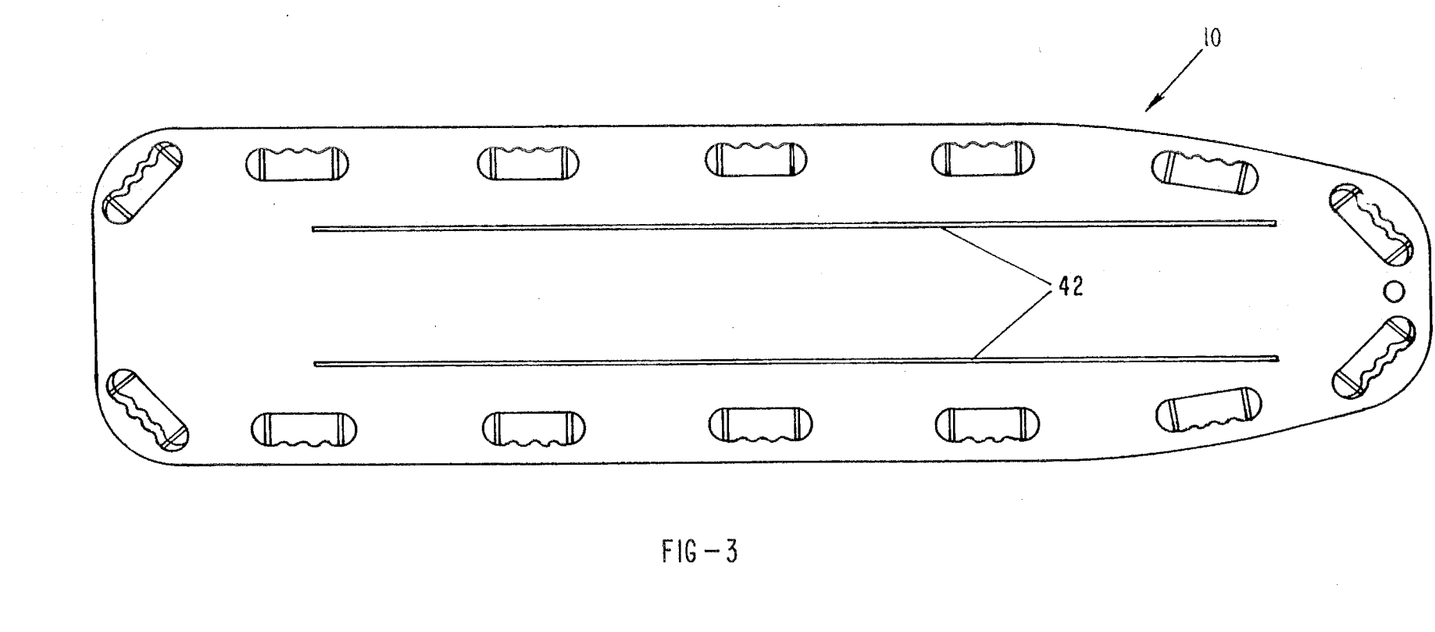
FIG. 3 is a bottom view of the preferred embodiment.
Figure 4:
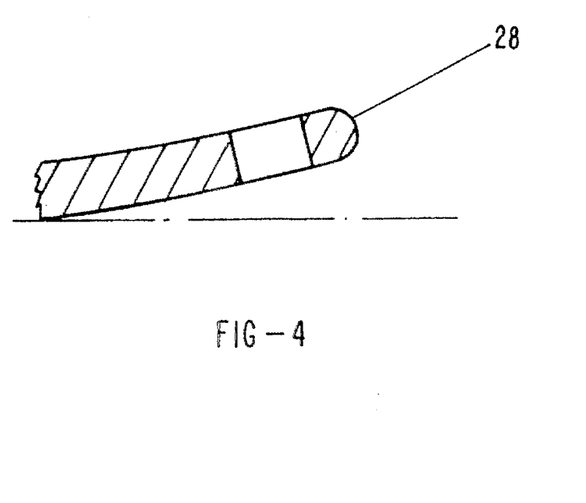
FIG. 4 is a cut-away view of section A—A (shown as 100 in the drawings) of FIG. 1.
Figure 5:
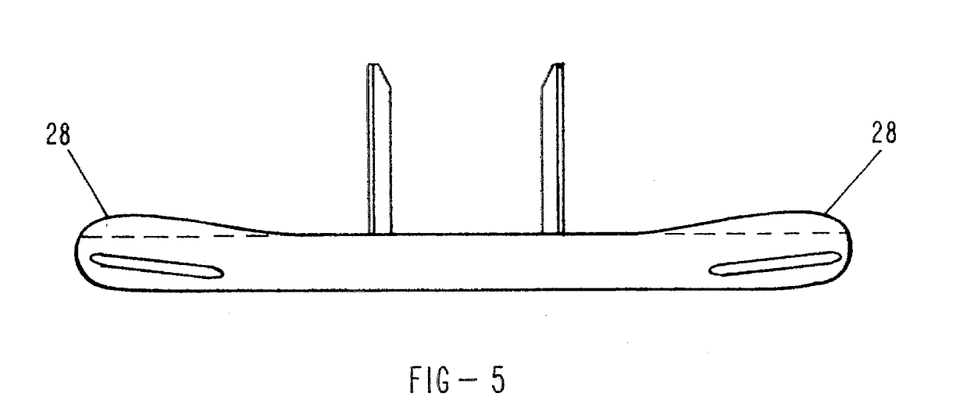
FIG. 5 is a front view of the preferred embodiment.

Referring to the side view of FIG. 2, the preferred immobilization device 10 additionally comprises side strap slots 33 and head and neck support brackets 40. Referring to the bottom view of FIG. 3, the preferred immobilization device 10 additionally comprises runners 42. Referring to the section view 100 of FIG. 4, the corners 28 are preferably upraised at an approximate seven degree angle. The front view of FIG. 5 also shows upraised corners 28.

Indentations 14 and 18 are approximately 0.25" deep, and padding 16 and 20 are semi-permanently attached therein. Grip holes 26 and 30 present no sharp edges, and have finger indentations on their outside edges to improve grip security. Straps for securing the patient may be provided to pegs 33 at each end of grip holes 26 and 30. The device may be stored by hanging from end hole 38.

The cervical restraint aspect of the invention is provided by slots 34 and 36 and brackets 40. There are preferably two rows of head support bracket slots 34, one on top and one below a patient's ears, and one row of neck support bracket slots 36. Each row has a plurality of slots on both sides of the patient's head and neck, permitting adjustment to the width of the patient's head and neck. Slots 34 and 36 are preferably 0.25" wide and 1.00" long, with approximately 0.25–0.50" between each slot in a row, and have velcro attachment strips 37.

Figure 6:
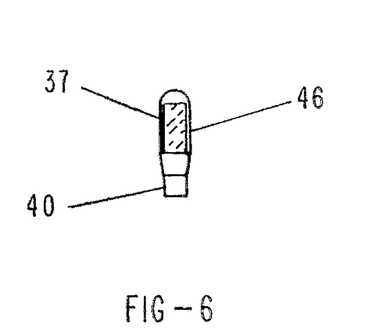
FIG. 6 is a side view of a head and neck support bracket.
Figure 7:
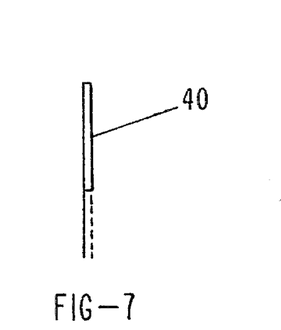
FIG. 7 is a front view of the bracket of FIG. 6.

Referring to FIGS. 6 and 7, the preferred head and neck support brackets 40 comprise two portions: slot engaging portion 44 and patient engaging portion 46. Portion 44 must lodge securely into head and neck support bracket slots 34 and 36. Portion 46 may be padded to increase patient restraint by increasing friction and to increase patient comfort.

Figure 8:
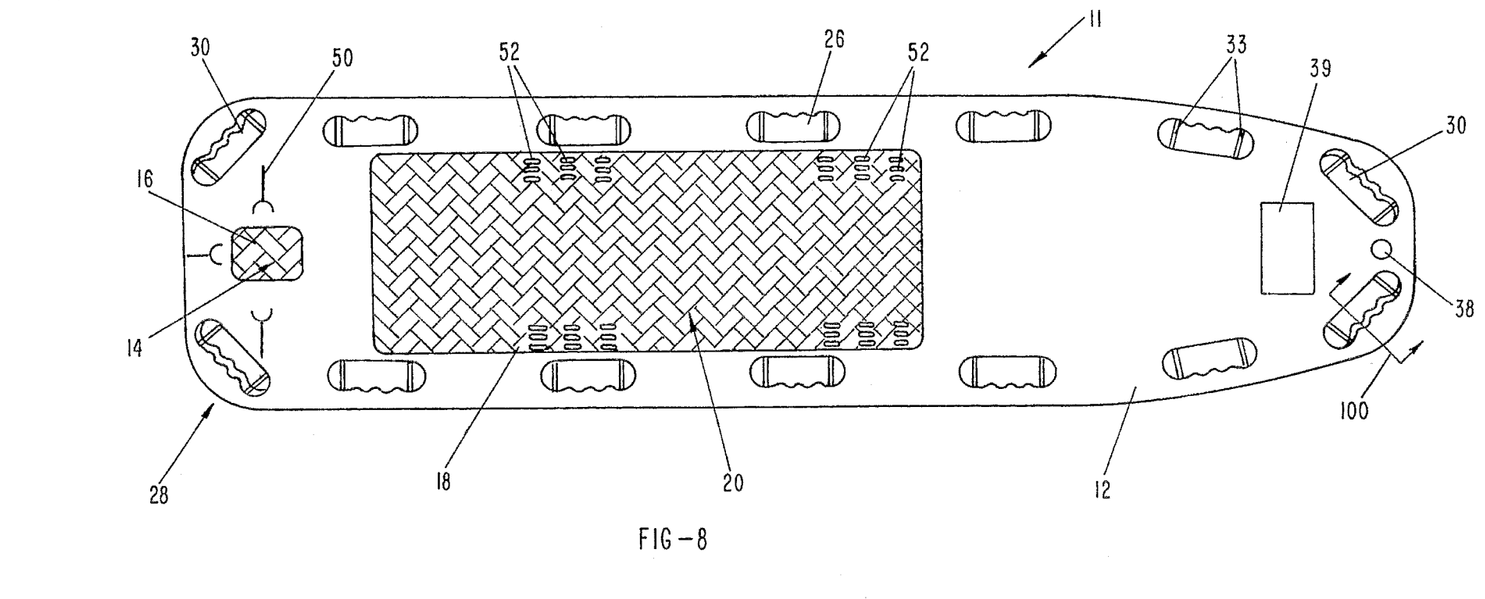
FIG. 8 is a top view of an alternative embodiment of the immobilization board of the invention.
Figure 9:
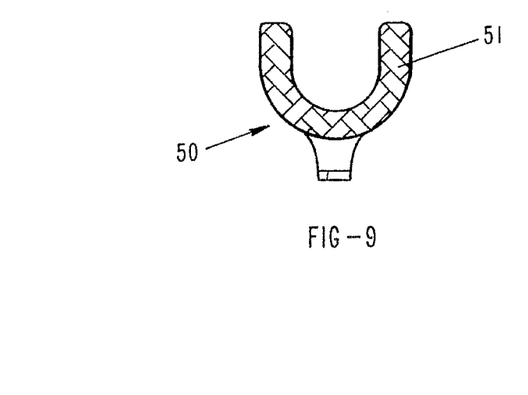
FIG. 9 is a front view of the preferred slidable head engagement arm of the alternative embodiment of FIG. 8.

An alternative embodiment of the board of the invention is show in top view in FIG. 8. Immobilization device 11 comprises a fiber-reinforced composite body 12, a beveled edge head indentation head padding 16, a beveled edge torso indentation 18, torso padding 20, edge molded grip holes 26, upraised corners 28, corner molded grip holes 30, end hole 38, and board identification and serial number zone 39, as in FIG. 1. Rather than using head and neck support bracket slots, the alternative employs slidable head engagement arms 50, preferably having a Y-shaped portion to engage a patient around the ears without covering the ears, which arms are secured to the head by conventional straps. A front view of the slidable head engagement arms 50 is shown in FIG. 9, with padding 51 to protect the head of the patient. The board additionally comprises torso support bracket slots 52, which operate to secure the torso to prevent twisting of the spinal column when torso support brackets (identical to head and neck support brackets) are placed therein. The torso support bracket slots and brackets are also useful when used with the head and neck support bracket slots and brackets of FIGS. 1–7.

Carbon-fiber-reinforced body 12 is preferably fabricated according to the following technique: A resin system is transferred, at low viscosity and pressure (such as 20–80 psi), into a closed mold which contains carbon-fiber reinforcements. The resin system is preferably prepared by premixing and placing the mixture into a resin injection pot, or alternatively by metering components from separate pots at the appropriate mix ratio to an in-line static mixer or mix zone. The mold may be filled under vacuum (such as 26–29 inches of Hg) to eliminate air from the mold space, to assist in resin injection, and to aid in the removal of volatiles. Resin system viscosity dictates whether pot and or mold heat is required. A viscosity of less than 100 cP at the injection temperature is desirable for best filling and wetting characteristics. After the mold is filled, it is sealed and heated in accordance with the appropriate cure schedule. The invention can then be removed from the mold and postcured as necessary.

The above process is an effective fabrication technique for the production of fiber-reinforced, high performance structural composites, especially at high fiber loadings (up to 70% fiber content) with low void volume. Resins useful in producing the invention are available from, for example, Shell Chemical Company. The invention can be fabricated by this technique to consistently produce a product at close tolerances with good surface finish on all surfaces, without the need for a gel coat. This is vital to minimize the risk of injury from burrs and the like.

The ends, edges, and bottom of the board may be fitted with protective strips or coverings to further protect the board from damages. The board may also be provided with a protective coating (preferably polyurethane) to further protect the board.

The invention satisfies the following medical requirements:

a) Patients and rescuers are protected from certain undesirable contacts. The turned up corners or ends provide easy hand-hold access (avoiding contact with ground-level gravel and glass fragments) and help to keep the patient centered on the board. The body support padding increases lateral restraint by increasing friction.

b) Patients are more comfortable during long periods of restraint. This is accomplished primarily by the support padding in the head and torso areas.

c) Patients may be x-rayed without having to be removed from the board. The materials comprising the composite board have low molecular weight (primarily carbon) and are relatively thin. The foam core adds bending stiffness to the structure while enabling a low mass profile. Areas which must be recessed to receive the support padding preferably have tapered edges which never come to a vertical edge. This avoids x-ray shadows from being created in areas covered by the patient's body.

d) Patients may be examined while the cervical immobilization device is in place. The composite head and neck support brackets enable trauma workers to secure a patient's head and neck while permitting physician access around the ears and sides of the head.

e) Emergency worker strain is reduced. Current boards weigh up to eighteen pounds and are often bulky and awkward to move, especially when stacked for moving or storing. Wood boards often have splinters and plastic boards often have burrs, especially after wear. The present invention weighs approximately seven to nine pounds (but can carry up to 700 pounds without cracking, measured with the board suspended from the corner grip holes), has lifting handles that are easily used, and will not splinter.

f) Patient movement during transport is minimized. The low thickness board profile enables the patient to be placed on the board with minimum lifting and a low probability of bumping during transfer to and from the board. Also, the upturned corner hand holds allow trauma crews to lift the board with the patient directly from flat on the ground with confidence and without having to tilt or rock the board to gain finger access to hand holds. The high stiffness skin provides the necessary stiffness to prevent a 300 pound patient from moving during crew walking or transfer to or from vehicles.

g) Life cycle costs to medical organizations are minimized. The composite board is very tolerant to moisture, fluids, and abrasion, and can be refurbished when burrs form. The expected life will be five to ten years, considerably longer than conventional boards.

h) The potential for bacterial contamination and concomitant spread of contaminants to patients is minimized. With the high tolerance to moisture and abrasion, the composite board surface remains washable and easily disinfected. Surface porosity is minimized. The support padding is easily removed for cleaning or replacement. The beveled recesses for the padding is easily cleanable, having no sharp corners. The pads also help prevent direct damage to the boards, again increasing their life expectancy.

i) The board is particularly well suited for military and air rescue operations because of its ability to be manufactured as fire resistant and its light weight characteristics, and for mountain and ski rescue operations because it is light weight.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents.

What is claimed is:

1. A spinal and cervical immobilization apparatus comprising:

a board on which a body of a patient is placed and which comprises a plurality of bifurcated rows of interior bracket slots disposed at an end of said board, each half of said bifurcated rows comprising a plurality of said interior bracket slots; and a plurality of head and neck support brackets, each comprising a bracket slot engagement portion and a patient engagement portion.

2. The apparatus of claim 1 wherein said board comprises a unitary fiber-reinforced composite.

3. The apparatus of claim 2 wherein said board is resin transfer molded.

4. The apparatus of claim 1 wherein said board is 1.75" or less in thickness, weighs nine pounds or less, and is capable of bearing a 700 pound load without cracking.

5. The apparatus of claim 1 wherein corners of said board are upturned.

6. The apparatus of claim 5 wherein said corners are rounded and comprise molded grip holes therein.

7. The apparatus of claim 6 wherein said board comprises a plurality of molded grip holes disposed near the edges thereof, said grip holes comprising indentations for fingers of persons carrying said board and patient, and wherein said grip holds in said corners have an angular orientation.

8. The apparatus of claim 1 wherein said board comprises beveled indentations for the head and torso of the patient.

9. The apparatus of claim 8 wherein said apparatus additionally comprises padding means in said indentations, said padding means being selected from the group consisting of permanent padding, semi-permanent padding, and removably placeable padding.

10. The apparatus of claim 1 wherein said board comprises a plurality of bifurcated rows of bracket slots disposed at a central portion of said board and wherein said apparatus additionally comprises a plurality of torso support brackets, each comprising a bracket slot engagement portion and a patient engagement portion.

11. A spinal immobilization apparatus comprising a board on which a body of a patient is placed comprising a resin transfer molded, unitary fiber-reinforced composite, having a thickness of 1.75" or less and a weight of nine pounds or less.

12. The apparatus of claim 11 wherein said apparatus additionally comprises a cervical immobilization device comprising:
   a plurality of bifurcated rows of bracket slots disposed at an end of said board; and
   a plurality of head and neck support brackets, each comprising a bracket slot engagement portion and a patient engagement portion.

13. The apparatus of claim 11 wherein said board comprises a plurality of bifurcated rows of bracket slots disposed at a central portion of said board and wherein said apparatus additionally comprises a plurality of torso support brackets, each comprising a bracket slot engagement portion and a patient engagement portion.

14. The apparatus of claim 11 wherein said board additionally comprises a cervical immobilization device comprising a plurality of carbon fiber slidable head and neck engagement means.

15. The apparatus of claim 14 wherein said slidable head and neck engagement means comprise a slidable patient engagement arm comprising a Y-shaped portion engaging a patient around an ear of the patient.

16. The apparatus of claim 11 wherein corners of said board are upturned.

17. The apparatus of claim 16 wherein said corners are rounded and comprise molded grip holes therein.

18. The apparatus of claim 17 wherein said board comprises a plurality of molded grip holes disposed near the edges thereof, said grip holes comprising indentations for fingers of persons carrying said board and patient, wherein said rounded corners comprise molded grip holes at an angular orientation of 20 degrees or greater.

19. The apparatus of claim 11 wherein said board comprises beveled indentations for the head and torso of the patient.

20. The apparatus of claim 19 wherein said apparatus additionally comprises padding means in said indentations, said padding means being selected from the group consisting of permanent padding, semi-permanent padding, and removably placeable padding.

21. A spinal immobilization apparatus comprising a board on which a body of a patient is placed comprising upturned corners beveled upward from a plane formed by a base of said board and molded grip holes disposed in said upturned corners.

22. The apparatus of claim 21 wherein said apparatus additionally comprises a cervical immobilization device comprising:
   a plurality of bifurcated rows of interior bracket slots disposed at an end of said board, each half of said bifurcated rows comprising a plurality of said interior bracket slots; and
   a plurality of head and neck support brackets, each comprising a bracket slot engagement portion and a patient engagement portion.

23. The apparatus of claim 21 wherein said board comprises a plurality of bifurcated rows of bracket slots disposed at a central portion of said board and wherein said apparatus additionally comprises a plurality of torso support brackets, each comprising a bracket slot engagement portion and a patient engagement portion.

24. The apparatus of claim 21 wherein said board additionally comprises a cervical immobilization device comprising a plurality of carbon fiber slidable head and neck engagement means.

25. The apparatus of claim 24 wherein said slidable head and neck engagement means comprise a slidable patient engagement arm comprising a Y-shaped portion engaging a patient around an ear of the patient.

26. The apparatus of claim 21 wherein said board comprises a unitary fiber-reinforced composite.

27. The apparatus of claim 26 wherein said board is resin transfer molded.

28. The apparatus of claim 21 wherein said board is 1.75" or less in thickness, weighs nine pounds or less, and is capable of bearing a 700 pound load without cracking.

29. The apparatus of claim 21 wherein said board comprises a plurality of molded grip holes disposed near the edges thereof, said grip holes comprising indentations for fingers of persons carrying said board and patient, and wherein said grip holes in said corners have an angular orientation of 20 degrees or greater.

30. The apparatus of claim 21 wherein said board comprises beveled indentations for the head and torso of the patient.

31. The apparatus of claim 30 wherein said apparatus additionally comprises padding means in said indentations, said padding means being selected from the group consisting of permanent padding, semi-permanent padding, and removably placeable padding.

32. A spinal immobilization apparatus comprising a board on which a body of a patient is placed comprising a plurality of molded grip holes disposed near the edges thereof, said grip holes comprising indentations for fingers of persons carrying said board and patient, wherein corners of said board are rounded, upturned, beveled upward from a plane formed by a base of said board, and comprise said molded grip holes therein.

33. The apparatus of claim 32 wherein said apparatus additionally comprises a cervical immobilization device comprising:
   a plurality of bifurcated rows of interior bracket slots disposed at an end of said board, each half of said bifurcated rows comprising a plurality of said interior bracket slots; and
   a plurality of head and neck support brackets, each comprising a bracket slot engagement portion and a patient engagement portion.

34. The apparatus of claim 32 wherein said board comprises a plurality of bifurcated rows of bracket slots disposed at a central portion of said board and wherein said apparatus additionally comprises a plurality of torso support brackets, each comprising a bracket slot engagement portion and a patient engagement portion.

35. The apparatus of claim 32 wherein said board additionally comprises a cervical immobilization device comprising a plurality of carbon fiber slidable head and neck engagement means.

36. The apparatus of claim 35 wherein said slidable head and neck engagement means comprise a slidable patient engagement arm comprising a Y-shaped portion engaging a patient around an ear of the patient.

37. The apparatus of claim 32 wherein said board comprises a unitary fiber-reinforced composite.

38. The apparatus of claim 37 wherein said board is resin transfer molded.

39. The apparatus of claim 32 wherein said board is 1.75" or less in thickness, weighs nine pounds or less, and is capable of bearing a 700 pound load without cracking.

40. The apparatus of claim 32 wherein said corners of said board are upturned.

41. The apparatus of claim 40 wherein said corners are rounded and comprise molded grip holes therein.

42. The apparatus of claim 32 wherein said board comprises beveled indentations for the head and torso of the patient.

43. The apparatus of claim 42 wherein said apparatus additionally comprises padding means in said indentations, said padding means being selected from the group consisting of permanent padding, semi-permanent padding, and removably placeable padding.

44. A spinal immobilization apparatus comprising:

a board on which a body of a patient is placed comprising beveled indentations for the head and torso of the patient; and padding means in said indentations, said padding means being selected from the group consisting of permanent padding, semi-permanent padding, and removably placeable padding.

45. The apparatus of claim 44 wherein said apparatus additionally comprises a cervical immobilization device comprising:

a plurality of bifurcated rows of bracket slots disposed at an end of said board; and a plurality of head and neck support brackets, each comprising a bracket slot engagement portion and a patient engagement portion.

46. The apparatus of claim 44 wherein said board comprises a plurality of bifurcated rows of bracket slots disposed at a central portion of said board and wherein said apparatus additionally comprises a plurality of torso support brackets, each comprising a bracket slot engagement portion and a patient engagement portion.

47. The apparatus of claim 44 wherein said board additionally comprises a cervical immobilization device comprising a plurality of slidable head and neck engagement means.

48. The apparatus of claim 47 wherein each of said slidable head and neck engagement means comprises a slidable patient engagement arm comprising a Y-shaped portion engaging a patient around an ear of the patient.

49. The apparatus of claim 44 wherein said board comprises a unitary fiber-reinforced composite.

50. The apparatus of claim 49 wherein said board is resin transfer molded.

51. The apparatus of claim 44 wherein said board is 1.75" or less in thickness, weighs nine pounds or less, and is capable of bearing a 700 pound load without cracking.

52. The apparatus of claim 44 wherein corners of said board are upturned.

53. The apparatus of claim 52 wherein said corners are rounded and comprise molded grip holes therein.

54. The apparatus of claim 44 wherein said board comprises a plurality of molded grip holes disposed near the edges thereof, said grip holes comprising indentations for fingers of persons carrying said board and patient.

55. A method of immobilizing a patient's spinal and cervical areas, the method comprising the steps of:

a) moving the patient onto a board comprising a plurality of bifurcated rows of interior bracket slots at an end thereof, each half of the bifurcated rows comprising a plurality of the interior bracket slots;

b) placing a head and neck of the patient at a bifurcation of the rows; and c) setting head and neck support brackets in the slots such that both sides of the head and neck are engaged by the brackets.

56. The method of claim 55 additionally comprising the steps of:

d) placing a torso of the patient at a bifurcation of a plurality of bifurcated rows of bracket slots at a central portion of the board; and e) setting torso support brackets in the slots such that both sides of the torso are engaged by the brackets.

57. A spinal immobilization apparatus comprising:

a board on which a body of a patient is placed comprising one or more indentations for the body of the patient; and padding means in said one or more indentations, said padding means being selected from the group consisting of permanent padding, semi-permanent padding, and removably placeable padding.

* * * * *